United States Patent
Molina et al.

(10) Patent No.: US 11,406,323 B2
(45) Date of Patent: Aug. 9, 2022

(54) METHOD AND SYSTEM FOR MONITORING SLEEP QUALITY

(71) Applicant: KONINKLIJKE PHILIPS N.V., Eindhoven (NL)

(72) Inventors: Gary Nelson Garcia Molina, Madison, WI (US); Cristhian Mauricio Potes Blandon, Salem, NH (US); Pedro Miguel Ferreira Dos Santos Da Fonseca, Borgerhout (BE); Bryan Conroy, Garden City South, NY (US); Minnan Xu, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 56 days.

(21) Appl. No.: 16/628,186

(22) PCT Filed: Jul. 10, 2018

(86) PCT No.: PCT/EP2018/068600
§ 371 (c)(1),
(2) Date: Jan. 2, 2020

(87) PCT Pub. No.: WO2019/011888
PCT Pub. Date: Jan. 17, 2019

(65) Prior Publication Data
US 2020/0146619 A1    May 14, 2020

Related U.S. Application Data

(60) Provisional application No. 62/530,635, filed on Jul. 10, 2017.

(51) Int. Cl.
*A61B 5/00* (2006.01)
*A61B 5/0205* (2006.01)

(52) U.S. Cl.
CPC .......... *A61B 5/4815* (2013.01); *A61B 5/0205* (2013.01); *A61B 5/4812* (2013.01); *A61B 5/7235* (2013.01)

(58) Field of Classification Search
CPC ... A61B 5/4815; A61B 5/4812; A61B 5/0205; A61B 5/7235
See application file for complete search history.

(56) References Cited

U.S. PATENT DOCUMENTS

2009/0005652 A1   1/2009   Kurtz
2012/0029378 A1   2/2012   Low
(Continued)

FOREIGN PATENT DOCUMENTS

WO   2006048852 A1   5/2006
WO   2016200233 A1   12/2016

OTHER PUBLICATIONS

International Search Report and Written Opinion, International Application No. PCT/EP2018/068600, dated Oct. 18, 2018.
(Continued)

*Primary Examiner* — Michael W Kahelin
*Assistant Examiner* — Naveed R. Kolia

(57) ABSTRACT

A system (400) for monitoring an individual's sleep includes: (i) a patient monitor (410) configured to obtain a patient waveform, the patient waveform comprising information representative of a vital statistic of the patient; a processor (420) in communication with the patient monitor and configured to: (i) process the patient waveform to generate a segmented waveform; (ii) extract at least one feature from a segment of the waveform in a time domain and/or at least one feature from the segment of the waveform in the frequency domain; (iii) classify, using the at least one extracted feature, a sleep stage of the patient for the segment of the waveform; and (iv) generate, from classified sleep stages for a plurality of segments of the waveform, a sleep
(Continued)

quality measurement; and a user interface (480) configured to report the generated sleep quality measurement.

30 Claims, 3 Drawing Sheets

(56) References Cited

U.S. PATENT DOCUMENTS

| | | | |
|---|---|---|---|
| 2012/0179061 A1* | 7/2012 | Ramanan | A61B 5/4809 600/538 |
| 2013/0046151 A1* | 2/2013 | Bsoul | A61B 5/4806 600/301 |
| 2015/0265207 A1 | 9/2015 | Wu et al. | |
| 2017/0055899 A1 | 3/2017 | Bandyopadhyay et al. | |
| 2020/0178892 A1* | 6/2020 | Maslik | A61B 5/0205 |

OTHER PUBLICATIONS

R. S. Bourne, C. Minelli, G. H. Mills, and R. Kandler, "Clinical review: Sleep measurement in critical care patients: research and clinical implications.," Crit. Care, vol. 11, No. 4, p. 226, 2007.

O. Dogan, S. Ertekin, and S. Dogan, "Sleep quality in hospitalized patients.," J. Clin. Nurs., vol. 14, pp. 107-113, 2005.

B. B. Kamdar, D. M. Needham, and N. A. Collop, "Sleep deprivation in critical illness: Its Role in Phisycal and Phychological Recovery," J Intensive Care Med., vol. 27, No. 2, pp. 97-111, 2012.

M. Basner, B. Griefahn, U. Müller, G. Plath, and A. Samel, "An ECG-based algorithm for the automatic identification of autonomic activations associated with cortical arousal.," Sleep, vol. 30, No. 10, pp. 1349-1361, 2007.

S. Babaeizadeh, D. P. White, S. D. Pittman, and S. H. Zhou, "Automatic detection and quantification of sleep apnea using heart rate variability.," J. Electrocardiol., vol. 43, No. 6, pp. 535-541, 2010.

* cited by examiner

METHOD AND SYSTEM FOR MONITORING SLEEP QUALITY

This application is the U.S. National Phase application under 35 U.S.C. § 371 of International Application No. PCT/EP2018/068600, filed on 10 Jul. 2018, which claims the benefit of U.S. Provisional Application No. 62/530,635, filed 10 Jul. 2017. These applications are hereby incorporated by reference herein.

FIELD OF THE INVENTION

The present disclosure is directed generally to methods and systems for monitoring or quantifying sleep.

BACKGROUND

Sleep quality is an important metric in many different environments, including in the home and in hospital settings. Knowing how much sleep an individual gets, and the quality of that sleep, is actionable information for the individual or a caregiver.

In the hospital setting, for example, there is a need to monitor sleep quality in patients due to the adverse effects of poor sleep quality on patient outcomes. Information about sleep quality can be used to adjust a patient's therapy, to plan patient care activities, to monitor patient recovery, and to help clinicians identify effective strategies that promote sleep and recovery. These modifications to patient care may also decrease complications associated with sleep deprivation.

Among the factors that can affect sleep quality in a hospital setting are environmental factors such as high light and noise levels, condition-related factors, and intervention factors. As an example, patients in an intensive care unit may experience as many as 40 to 60 interruptions every night due to patient care activities such as vital sign measurement, equipment adjustment, wound care, and transportation. These sleep disruptions can adversely affect both short- and long-term patient outcomes, and can result in cognitive deficits, slower recovery, and lowered immune function. These in turn negatively affect sleep, thereby reinforcing the lack of sleep quality.

Previously methods for monitoring sleep quality require expensive equipment or are obtrusive and inaccurate. Polysomnography, for example, is typically performed at a sleep disorder unit within a hospital or at a sleep center, and requires specialized equipment and a sleep technician. Actigraphy can measure sleep quality, but periods of inactivity are typically scored as sleep even when the patient is not sleeping.

SUMMARY OF THE INVENTION

There is a continued need for methods and systems that accurately monitor or quantify sleep without ex pensive or intrusive equipment.

The present disclosure is directed to inventive methods and systems for sleep monitoring. Various embodiments and implementations herein are directed to a system that utilizes patient data such as cardiovascular and/or respiratory waveforms to monitor and quantify patient sleep quality. The system extracts features from the patient data in the time and/or frequency domains, and classifies the information into one of a plurality of possible sleep stages, including wakefulness, REM, slow wave sleep, and shallow sleep stages. The information is used to provide one or more objective measurements of the quality of sleep, including a quality sleep index, total sleep time, sleep efficiency, sleep onset latency, sleep fragmentation, and/or other metrics. According to an embodiment, information about a patient's sleep stage is utilized for treatment options in real-time, and to analyze the effectiveness of therapies and treatments. Among other applications, information about a patient's sleep stage can be utilized to minimize patient-clinician interactions during periods of sleep, and to analyze the effect of medications and other therapies or interventions on sleep quality and other sleep metrics.

Generally, in one aspect, a system for monitoring a patient's sleep is provided. The system includes: a patient monitor configured to obtain a patient waveform, the patient waveform comprising information representative of a vital statistic of the patient; a processor in communication with the patient monitor and configured to: (i) process the patient waveform to generate a segmented waveform; (ii) extract at least one feature from a segment of the waveform in a time domain and/or at least one feature from the segment of the waveform in the frequency domain; (iii) classify, using the at least one extracted feature, a sleep stage of the patient for the segment of the waveform; and (iv) generate, from classified sleep stages for a plurality of segments of the waveform, a sleep quality measurement; and a user interface configured to report the generated sleep quality measurement.

According to an embodiment, the patient waveform is a cardiovascular waveform and/or a respiratory waveform.

According to an embodiment, the processor is further configured to generate, based on the generated sleep quality measurement, an intervention measure or prediction based on one or more of the patient's sleep stage and the generated sleep quality index.

According to an embodiment, the generated sleep quality measurement is a numerical value between 0 and 1 and/or 0 and 100, inclusive.

According to an embodiment, the processor is further configured to integrate the generated sleep quality measurement with additional data about the patient to generate integrated data.

In another aspect, a computerized method for monitoring a patient's sleep is provided. The method includes the steps of: (i) providing a sleep monitoring system comprising a patient monitor configured to obtain a patient waveform comprising information representative of a vital statistic of the patient, a processor in communication with the patient monitor, and a user interface; (ii) receiving, by the processor, the patient waveform from the patient monitor; (iii) processing, by the processor, the patient waveform to generate a segmented waveform; (iv) extracting, by the processor, at least one feature from a segment of the waveform in a time domain and/or extracting, by the processor, at least one feature from the segment of the waveform in the frequency domain; (v) classifying, by the processor using the at least one extracted feature, a sleep stage of the patient for the segment of the waveform; (vi) generating, by the processor from classified sleep stages for a plurality of segments of the waveform, a sleep quality measurement; and (vii) reporting, via the user interface, the generated sleep quality measurement.

According to an embodiment, the method further comprises the step of modifying, based on a classified sleep stage, a treatment for the patient.

According to an embodiment, the method further comprises the step of identifying, based on the generated sleep quality measurement, a treatment for the patient.

According to an embodiment, the method further comprises the step of identifying, based on the generated sleep quality measurement and/or on a plurality of classified sleep stages, an environmental factor affecting the patient's sleep quality.

According to an embodiment, the method further comprises the step of integrating the generated sleep quality measurement with additional data about the patient to generate integrated data.

According to an embodiment, the method further comprises the step of generating, based on the generated sleep quality measurement, an intervention measure or prediction based on one or more of the patient's sleep stage and the generated sleep quality index.

According to an embodiment, the generated sleep quality measurement is reported graphically.

According to an embodiment, the reporting step comprises reporting a classified sleep stage.

In various implementations, a processor or controller may be associated with one or more storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of a system for sleep monitoring. More generally, Applicant has recognized and appreciated that it would be beneficial to provide a system that analyzes patient data such as cardiovascular and/or respiratory waveforms and extracts features in the time and/or frequency domains, and classifies the information into one of a plurality of possible sleep stages, including wakefulness, REM, slow wave sleep, and shallow NREM sleep stages. According to an embodiment, the information is used to provide one or more objective measurements of the quality of sleep, including a quality sleep index, total sleep time, sleep efficiency, sleep onset latency, sleep fragmentation, and/or other metrics. According to an embodiment, information about a patient's sleep stage could be utilized for treatment options in real-time, and to analyze the effectiveness of therapies and treatments.

Figure 1:
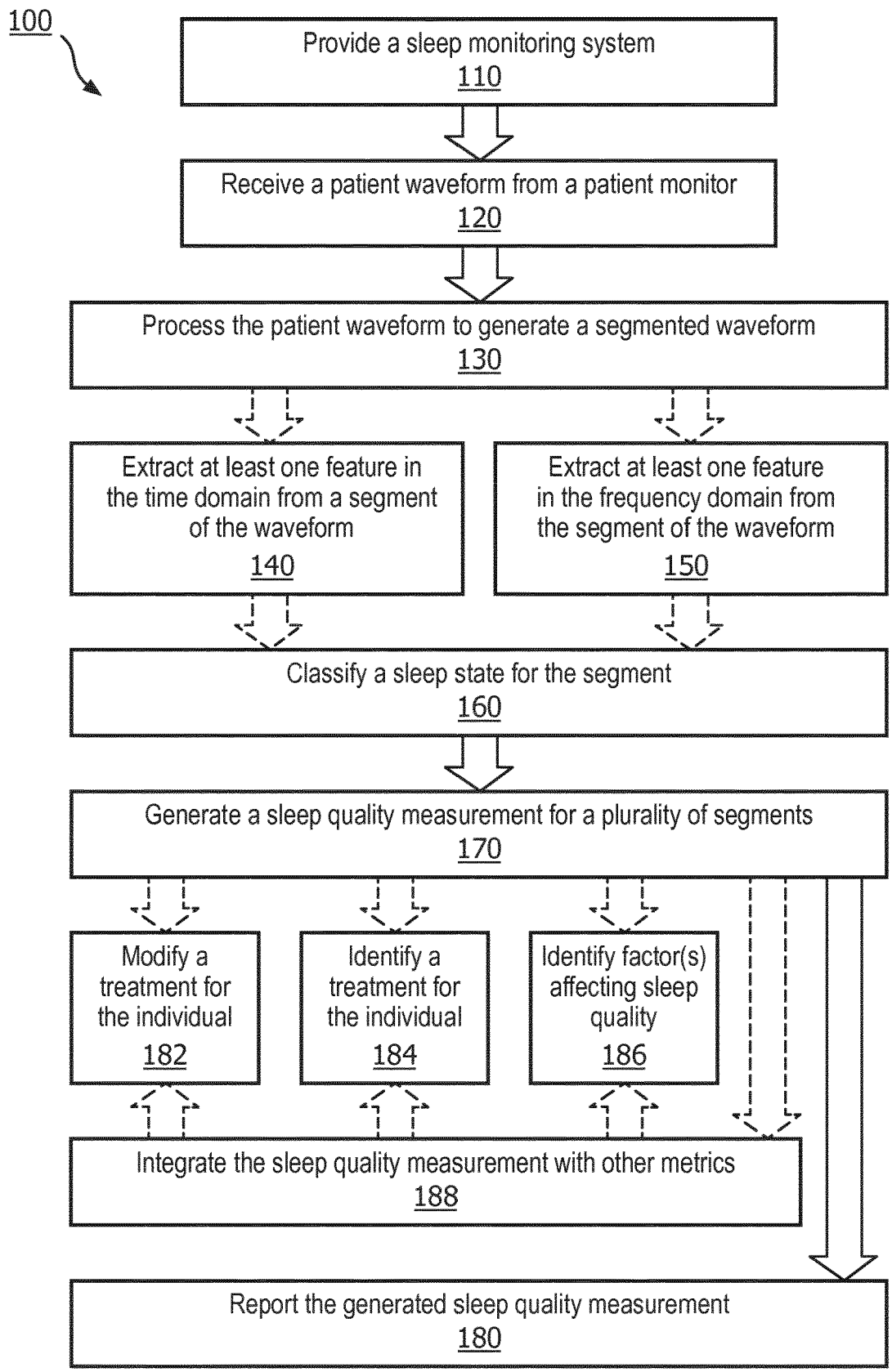
FIG. 1 is a flowchart of a method for sleep monitoring, in accordance with an embodiment.

Referring to FIG. 1, in one embodiment, is a flowchart of a method 100 for sleep monitoring as disclosed or otherwise envisioned herein. At step 110 of the method, a system for sleep analysis or monitoring is provided. The sleep monitoring system can be any of the systems described or otherwise envisioned herein. For example, the sleep monitoring system may comprise a patient monitor configured to obtain a patient waveform comprising information representative of a vital statistic of the patient, a processor in communication with the patient monitor, and a user interface, among many other elements or components.

At step 120 of the method, the system obtains or receives a patient waveform. According to an embodiment, the system obtains the patient waveform from a patient monitor, which may be directly connected to the system, or may be remotely located from the system and in communication with the system via a wired and/or wireless network. For example, the patient monitor may be any device, wearable, sensor, or other element configured to or capable of obtaining data about an individual. The patient monitor may be in direct communication with the individual, or may obtain information via an indirect contact such as video, IR, motion detector, or any other type of direct or indirect sensor.

According to an embodiment, the patient waveform is a cardiovascular waveform such as an electrocardiogram (ECG) or any other form of measuring an individual's electrophysiological activity (such as electromyography, electroencephalography, electro-oculography, and/or electronystagmography, among many others), blood pressure measurement, and/or a photoplethysmogram (PPG). The patient waveform may also or alternatively be a respiratory waveform such as a respiratory rate or other respiratory measurement. According to an embodiment, one or more of these patient waveforms are routinely monitored in a medical setting, and thus could be obtained, for example, from an existing patient monitor in a hospital or other medical care setting.

According to an embodiment, the patient waveform is patient movement obtained by an actigraph measurement device. The patient may wear or be exposed to an actimetry sensor that measures movements that the sensor undergoes. The actimetry sensor can then provide the measurements to the system, including as a waveform.

According to an embodiment, the received or obtained waveform may be analyzed immediately, and/or may be stored for subsequent analysis. As one example, a time period may be analyzed pursuant to the methods described herein only upon request. A physician, nurse, or other medical care professional may request that the system provide a sleep quality metric for the previous night, and the system will retrieve the patient waveforms from a storage device which is a component of the system or otherwise in wired and/or wireless communication with the system, and will analyze the retrieved patient waveforms to produce the requested information.

At step 130 of the method, the system processes the received or obtained patient waveform to generate a segmented waveform. According to an embodiment, the system segments the received waveform into two or more segments. The segment size can be predetermined or pre-programmed, can be based in whole or in part on machine learning, or can be set by a user or the patient. According to an embodiment, the system performs one or more analyses before and/or after segmentation of the waveform. For example, a signal processing unit or module of the system may remove, reduce, or otherwise modify or adjust noise in the patient waveform. The signal processing unit or module of the system may remove, reduce, or otherwise modify or adjust trends in the patient waveform. In addition to these analyses and processes, many others are possible.

At step 140 of the method, the system extracts at least one feature from a segment of the waveform in a time domain. Similarly, at step 150 of the method, the system extracts at least one feature from the same segment of the waveform in a frequency domain. This can be repeated for multiple segments. According to an embodiment, waveform features include, but are not limited to, sympathetic/parasympathetic tone (RR-intervals, heart rate variability), spectral power across different frequency bands such as low, medium, and high, envelope of the signal, and cardio-respiratory coupling (pulse transit time), among many others.

According to an embodiment, the system performs both steps 140 and 150. Alternatively, the system may perform either step 140 or 150. For example, the system may only extract at least one feature from a segment of the waveform in a time domain, or may only extract at least one feature from a segment of the waveform in the frequency domain.

At step 160 of the method, the system classifies a sleep state or stage of the patient for the segment of the waveform using at least the extracted waveform features for that segment. The system may classify a single waveform segment, or may classify multiple waveform segments. According to an embodiment, the system inputs the extracted waveform features for one or more segments into a classifier module that classifies the segment into one or more of a plurality of different sleep states. According to an embodiment, the classifier module classifies a segment into one of a plurality of different sleep states based on which sleep state the extracted waveform features best fit into or otherwise match. This can be based on machine learning, can be based on predetermined or pre-programmed thresholds or bins, can be settings made by a patient and/or medical professional, and/or can be otherwise programmed or selected. According to an embodiment, the classifier module utilizes a neural network and/or logistic regression to classify the segmented waveform using at least the extracted waveform features for that segment.

According to an embodiment, the classifier module that classifies the segment into one or more of a plurality of different sleep states or stages such as awake (or wakefulness), stage 1 shallow sleep (stage 1 N1), stage 2 shallow sleep (stage 2 N2), stage 3 slow wave sleep (stage 3 SWS or N3), stage 4 slow wave sleep (stage 4 SWS or N3 (formerly called S4)), and rapid eye movement sleep (REM), although additional stages are possible. For example, the system may break one or more of these stages into one or more sub-stages. Alternatively, the system may combine one or more of these stages, such as combining stages 1 and 2 into a single stage, and combining stages 3 and 4 into a single stage.

Sleep cycles vary by individual and by setting. For example, on average an individual's first sleep cycle takes about 90 minutes, and then averages about 100 to 120 minutes per cycle after that, with about four to five sleep cycles a night. However, in a hospital setting where there are numerous interruptions, the patient's sleep cycles may not be near the averages proposed herein. Accordingly, the system is designed to recognize and classify sleep stages regardless of the position of the stage or segment within a detected or hypothesized sleep cycle.

At step 170 of the method, the system generates a sleep quality measurement from classified sleep states for a plurality of segments of the waveform. According to embodiment, the sleep quality measurement is a sleep quality index (SQI) that ranges between 0, representing a low (or no) sleep quality, and 1, representing a high sleep quality.

According to embodiment, the system may generate an SQI value or other sleep quality measurement in any one of a variety of different ways. For example, the system may utilize predetermined, pre-programmed, machine learned, or user-determined settings to evaluate sleep quality. For example, objective measurements of sleep quality may include, among many others, total duration, duration of one or multiple stages of sleep, efficiency of sleep, fragmentation of sleep, and the structure of sleep such as progression through one or more sleep cycles. One objective measurement may be based on the proper cycling of stages as the individual moves through one or more sleep cycles.

Accordingly, the SQI value or other sleep quality measurement may be based on one of these or other objective measurements of sleep quality. Alternatively, the SQI value or other sleep quality measurement may be based on multiple of these or other objective measurements of sleep quality. For example, the SQI value or other sleep quality measurement may utilize an initial starting value based on total duration of sleep, and then may alter or adjust that value based on additional measurements. The initial starting value may be increased if the individual properly cycled through stages in a sleep cycle, went through multiple sleep cycles, had unfragmented or uninterrupted sleep, or had other positive sleep experiences. The initial starting value may be decreased if the individual did not properly cycle through stages in a sleep cycle, went through too few sleep cycles, had fragmented or interrupted sleep, or had other negative sleep experiences. The initial starting value may be both increased and decreased by these or other measurements of sleep quality. In addition to the initial starting value methodology described herein, other methodologies for obtaining a SQI value or other sleep quality measurement are possible.

At step 180 of the method, the system reports the generated SQI value or other sleep quality measurement to the user. The generated sleep quality measurement may be provided using any method or system of conveying information. For example, the generated sleep quality measurement may be provided via a user interface, which may be a monitor, mobile device, laptop, desktop, wearable device, home computing device, or any other device. The generated sleep quality measurement may be provided as a visual/auditory or haptic cue. The generated sleep quality measurement may be provided as standalone information, and/or may be provided as information incorporated into other information about the system, about the patient, or about other information sources. For example, the generated sleep quality measurement may be displayed as an alert to indicate overall poor sleep quality, such as in a dashboard. As another example, the generated sleep quality measurement may be displayed as a continuous trend, including possibly aligned to one or more other clinical events or measurements.

Figure 2:
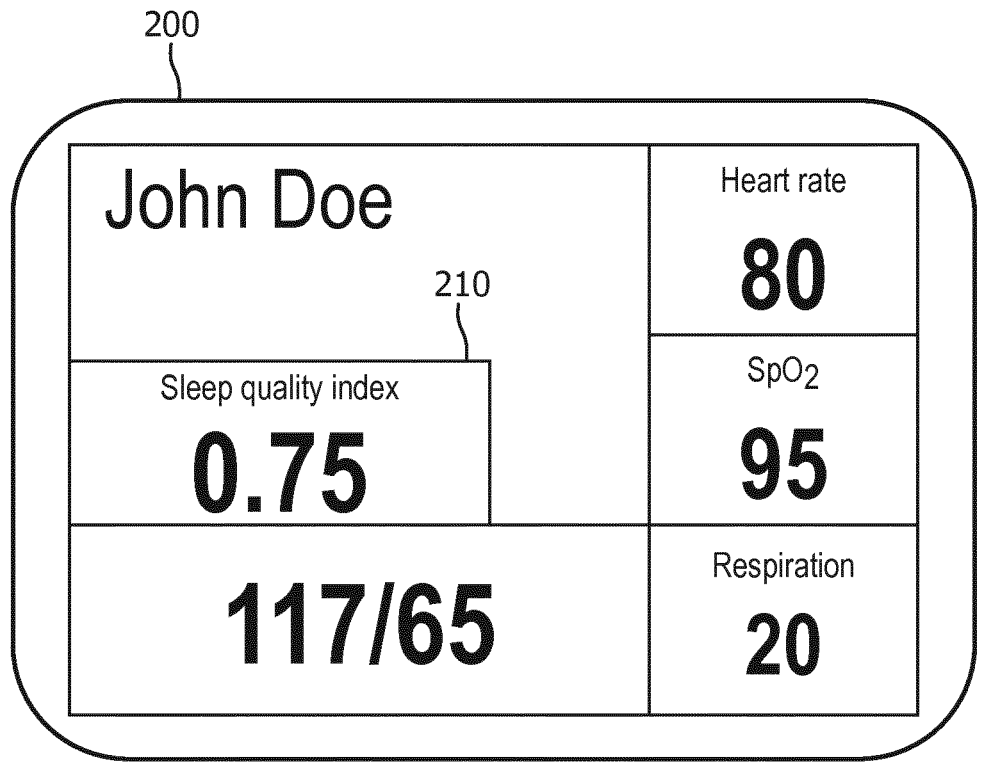
FIG. 2 is a schematic representation of a monitor display a sleep quality measurement, in accordance with an embodiment.

Referring to FIG. 2, in one embodiment, is a display 200 such as a patient monitor. The display comprises information about a plurality of metrics about the individual such as heart rate, $SpO_2$, respiration, blood pressure, and a sleep quality index 210, which is provided as a number between 0, representing a low (or no) sleep quality, and 1, representing a high sleep quality. Here, as just one non-restricting example, the patient has a sleep quality index of 0.75, which represents sleep quality for the current timeframe or the night before. According to another embodiment, the system may provide a sleep quality index number between 0 and 100, among many other possible representations. For example, the sleep quality index may be provided as a color or any other representation.

Figure 3:
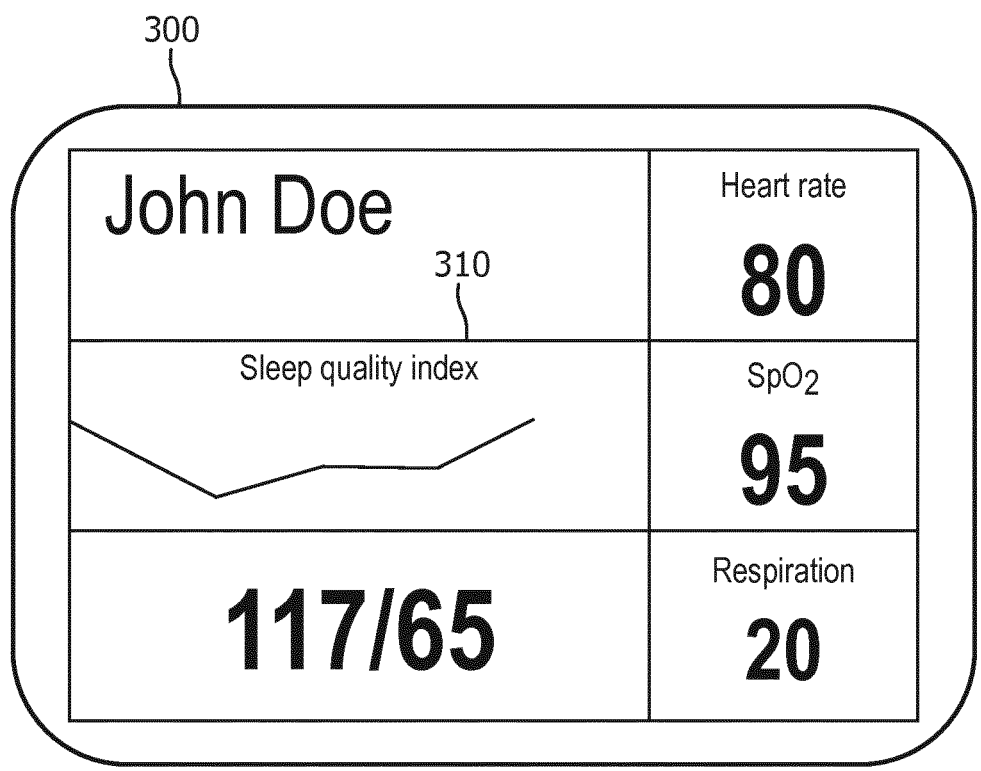
FIG. 3 is a schematic representation of a monitor display a sleep quality measurement, in accordance with an embodiment.

Referring to FIG. 3, in one embodiment, is a display 300 such as a patient monitor. The display comprises information about a plurality of metrics about the individual such as heart rate, $SpO_2$, respiration, blood pressure, and a sleep quality index 310, which is provided as a line graph. According to an embodiment, the line graph represents the current sleep quality index for the individual, and is presented as a number between 0, representing a low (or no) sleep quality, and 1, representing a high sleep quality. Accordingly, the sleep quality index may be updated periodically and/or continuously. In addition to these methods of display, many other mechanisms of display are possible.

At optional step 182 of the method, the system or a medical professional modifies a treatment for the individual based on a classified sleep state or stage. Similarly, at optional step 184 of the method, the system or a medical professional modifies a treatment for the individual based on the generated sleep quality measurement. According to an embodiment, the system or a medical professional observes or reviews a sleep state or stage, or the generated sleep quality measurement, to determine a course of action. For example, the system or a medical professional may determine that an intervention or treatment is necessary, or not necessary or warranted, if the individual is within a certain sleep stage or sleep quality, or if the individual has experienced a certain sleep stage or sleep quality within a relevant time frame. As just one example, the current sleep stage and/or sleep history can be used to reschedule or postpone a procedure or treatment such as blood pressure monitoring or other vital monitoring when that monitoring is not critical and if the sleep stage suggests that the patient should not be interrupted if possible. For example, some sleep stages, or a dynamic variation thereof, may indicate that the patient should not be interrupted in order to maximize sleep quality, while other sleep stages may be more open to interruption. As another example, the current sleep stage and/or sleep history can be used to accelerate or advance a procedure or treatment.

According to an embodiment, the user interface may include an interruptibility measure or prediction based on one or more of: (i) the user's current sleep stage; (ii) a predicted sleep stage in the imminent future; (iii) the necessity of a treatment; and (iv) the user's recent sleep quality index, among many other factors. For example, the interruptibility measure or prediction may include an objective number of current interruptibility, where a high number represents a good time frame for interruptibility while a low number represents a bad time frame for interruptibility, or vice versa. As another example, the interruptibility measure or prediction may include a countdown, timer, or predicted time frame in which the individual is more likely to be receptive to interruptions, and/or when interruptions are less likely to impact a sleep stage and/or the sleep quality index. As yet another example, the interruptibility measure or prediction may be a hypnogram which characterizes the sleep stage dynamics during the last few hours. The hypnogram can be, for example, a graph depicting the user's history of sleep/wake periods.

It has been reported in studies that a significant number of nocturnal interactions in medical care settings could be safely omitted. Additionally, it has been estimated that many patients are woken two to five times throughout the night, which interrupts sleep and contributes to difficulties falling back to sleep. These studies suggest that some of the interactions are performed as routine rather than based on clinical evidence and necessity. One way sleep disruptions resulting from patient-clinician interactions could be minimized is if clinicians knew the current patient's sleep stage, hypnogram, or other sleep information or history.

According to one embodiment, the patient's generated sleep quality index could be integrated with a risk score provided by a hemodynamic instability indicator to help clinicians plan the care of the patient that best promotes sleep and aid recovery. For example, cuff blood pressure is an important vital sign, but its measurement often interferes with sleep. This vital sign may not need to be measured for patients who are not at high risk of hemodynamic deterioration and do not have active cardiac problems. Accordingly, cuff blood pressure measurements could be scheduled according to the sleep stage and/or sleep quality index of the patient. For example, a cuff blood pressure measurement could be delayed if the patient is: (i) at low risk of hemodynamic instability; and (ii) experiencing an important sleep stage or has a low sleep quality index.

At optional step 186 of the method, the system, a medical professional, or other system or individual identifies an environmental factor affecting the individual's sleep quality based on the generated sleep quality measurement and/or on a plurality of classified sleep states. For example, a sleep stage and/or a generated sleep quality measurement may provide insight to the patient, medical professional, and/or patient's relatives about the effect of a medication, the effectiveness of the recovery process, and/or the effect of one or more interventions on the patient's sleep quality.

At optional step 188 of the method, the system, a medical professional, or other system or individual integrates generated sleep quality measurement with additional data about the patient to generate integrated data, and identifies or modifies, based on the integrated data, a treatment for the patient. For example, the generated sleep quality measurement may be combined with other vitals about the patient to produce a fine-tuned objective measurement of the patient's health, the effectiveness of the recovery process, and/or the effect of one or more interventions on the patient's sleep quality.

According to an embodiment, the sleep quality index is an important vital sign that, when integrated with other data collected from the medical setting, can be very powerful for identifying gaps in medical care. Data analytics can be applied to generate reports to identify factors that contribute to poor sleep for an individual patient or a population of patients. For example, these reports have the potential for addressing the following the effect of certain drugs and interventions on sleep patterns. Such a system can help clinicians identify ways to change care to promote sleep and recovery, thereby decreasing complications associated to sleep deprivation. As another example, these reports can help examine the relationship between sleep quality and patient recovery, which can help the medical setting understand the contribution of care-related sleep disruption to patient outcomes, such as patient recovery from critical illness, post-care cognition, physical and mental health, and more.

According to an embodiment, additional parameters related to sleep or sleep disturbances can be measured which also rely on cardiovascular and/or respiratory waveforms that are routinely acquired in a medical care setting. For example, one of these parameters is related to autonomic arousals, which can be measured from heart rate variability changes detected from cardiovascular waveforms. Arousals can be valuable indicators of sleep disruption and sleep fragmentation, and can give insights about endogenous factors such as health-related factors as well as exogenous factors such as noise that influence the quality of sleep. Another parameter is related to sleep-disordered breathing (SDB) disorders, such as sleep apnea. SDB is usually monitored with respiratory modalities such as respiratory flow, respiratory effort and $SpO_2$, but it has been shown that in the absence of these sensors, screening can be successfully performed with cardiovascular waveforms such as ECG. Monitoring these conditions can give additional insights into the condition of a hospitalized patient.

Figure 4:
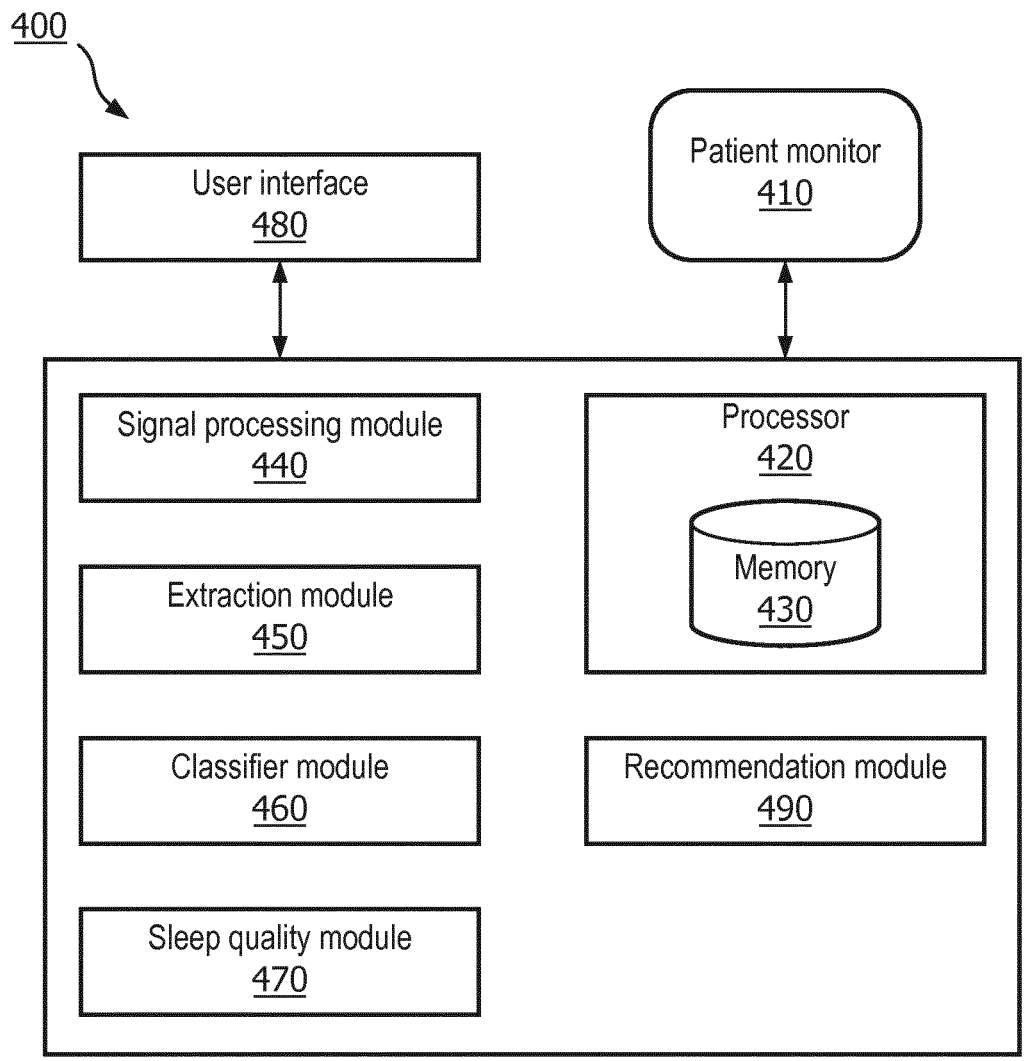
FIG. 4 is a schematic representation of a system for sleep monitoring, in accordance with an embodiment.

Referring to FIG. 4, in one embodiment, is a schematic representation of a system 400 for monitoring a patient's sleep. System 400 can comprise any of the elements, engines, database, processors, and/or other components described or otherwise envisioned herein. Although depicted as a single system in FIG. 4, it should be recognized that the system can comprise multiple components in multiple different locations. For example, one or more of the components may be remote from the system, and may be in communication with the system via a wired and/or wireless communication system, network or other communication means.

System 400 comprises a processor 420 which performs one or more steps of the method, and may comprise one or more of the engines or generators. Processor 420 may be formed of one or multiple modules, and can comprise, for example, a memory 430. Processor 420 may take any suitable form, including but not limited to a microcontroller, multiple microcontrollers, circuitry, a single processor, or plural processors. Memory 430 can take any suitable form, including a non-volatile memory and/or RAM. The non-volatile memory may include read only memory (ROM), a hard disk drive (HDD), or a solid state drive (SSD). The memory can store, among other things, an operating system. The RAM is used by the processor for the temporary storage of data. According to an embodiment, an operating system may contain code which, when executed by the processor, controls operation of one or more components of system 400.

System 400 comprises a patient monitor 410, which may be directly connected to the system, or may be remotely located from the system and in communication with the system via a wired and/or wireless network. For example, the patient monitor may be any device, wearable, sensor, or other element configured to or capable of obtaining data about an individual. The patient monitor may be in direct communication with the individual, or may obtain information via an indirect contact such as video, IR, motion detector, or any other type of direct or indirect sensor. The patient monitor 410 is configured to obtain or receive a patient waveform comprising information representative of a vital statistic of the patient. The patient waveform may be a cardiovascular waveform such as an electrocardiogram (ECG) or any other form of measuring an individual's electrophysiological activity (such as electromyography, electroencephalography, and/or electronystagmography, among many others), blood pressure measurement, and/or a photoplethysmogram (PPG). The patient waveform may also or alternatively be a respiratory waveform such as a respiratory rate or other respiratory measurement. The patient waveform may also or alternatively be an actigraph waveform.

System 400 comprises a user interface 480 which is configured to report a generated sleep quality measurement, sleep stage, and/or other information. The user interface 480 may be a monitor, mobile device, laptop, desktop, wearable device, home computing device, or any other device. The generated sleep quality measurement may be provided as a visual/auditory or haptic cue. The generated sleep quality measurement may be provided as standalone information, and/or may be provided as information incorporated into other information about the system, about the patient, or about other information sources. For example, the generated sleep quality measurement may be displayed as an alert to indicate overall poor sleep quality, such as in a dashboard. As another example, the generated sleep quality measurement may be displayed as a continuous trend, including possibly aligned to one or more other clinical events or measurements.

System 400 comprises a signal processing module 440, which segments the received waveform into two or more segments. The segment size can be predetermined or preprogrammed, can be based in whole or in part on machine learning, or can be set by a user or the patient. According to an embodiment, the system performs one or more analyses before and/or after segmentation of the waveform. For example, a signal processing unit or module of the system may remove, reduce, or otherwise modify or adjust noise in the patient waveform. The signal processing unit or module of the system may remove, reduce, or otherwise modify or adjust trends in the patient waveform. In addition to these analyses and processes, many others are possible System 400 comprises an extraction module 450, which extracts at least one feature from a segment of the waveform in a time domain, and extracts at least one feature from the same segment of the waveform in a frequency domain. This can be repeated for multiple segments. According to an embodiment, waveform features include, but are not limited to, sympathetic/parasympathetic tone (RR-intervals, heart rate variability), spectral power across different frequency bands such as low, medium, and high, envelope of the signal, and cardio-respiratory coupling (pulse transit time), among many others.

System 400 comprises a classifier module 460, which classifies a sleep state of the patient for the segment of the waveform using at least the extracted waveform features for that segment. The system may classify a single waveform segment, or may classify multiple waveform segments. According to an embodiment, the system inputs the extracted waveform features for one or more segments into a classifier module that classifies the segment into one or more of a plurality of different sleep states. According to an embodiment, the classifier module classifies a segment into one of a plurality of different sleep states based on which sleep state the extracted waveform features best fit into or otherwise match. This can be based on machine learning, can be based on predetermined or pre-programmed thresholds or bins, can be settings made by a patient and/or medical professional, and/or can be otherwise programmed or selected. According to an embodiment, the classifier module utilizes a neural network and/or logistic regression to classify the segmented waveform using at least the extracted waveform features for that segment.

System 400 comprises a sleep quality module 470, which generates a sleep quality measurement from classified sleep states for a plurality of segments of the waveform. According to embodiment, the system may generate a sleep quality measurement in any one of a variety of different ways. For example, the system may utilize predetermined, pre-programmed, machine learned, or user-determined settings to evaluate sleep quality. For example, objective measurements of sleep quality may include, among many others, total duration, duration of one or multiple stages of sleep, efficiency of sleep, fragmentation of sleep, and the structure of sleep such as progression through one or more sleep cycles. One objective measurement may be based on the proper cycling of stages as the individual moves through one or more sleep cycles.

System 400 may comprise a recommendation module 490, which provides information or insight to a patient or a medical professional about the individual and one or more possible interventions, treatments, or outcomes, among other aspects. For example, the recommendation module may generate a measure or prediction of the patient's sleep stage or quality and the effect an interruption may have, or the time frame in which an interruption should or should not occur to maximize a parameter of sleep. For example, the recommendation module may generate an intervention measure or prediction based on one or more of: (i) the user's current sleep stage; (ii) a predicted sleep stage in the imminent future; (iii) the necessity of a treatment; and (iv) the user's recent sleep quality index, among many other factors. The medical professional may utilize the intervention measure or prediction based to determine whether an intervention or treatment is necessary or warranted.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A system for monitoring a patient's sleep, the system comprising:
  a patient monitor configured to obtain a patient waveform, the patient waveform comprising information representative of a vital statistic of a patient;
  a tangible, non-transitory computer-readable medium that stores instructions;

a processor in communication with the patient monitor and adapted to execute the instructions to: (i) process the patient waveform to generate a segmented waveform; (ii) extract at least one feature from a segment of the patient waveform in a time domain and/or at least one feature from the segment of the patient waveform in a frequency domain; (iii) classify, using the at least one extracted feature, a sleep stage of the patient for the segment of the patient waveform; (iv) generate, from classified sleep stages for a plurality of segments of the patient waveform, a sleep quality index; and (v) generate an interruptibility measure comprising an objective number of current interruptibility from one or more of: the sleep stage of the patient; a predicted sleep stage; necessity of a patient sleep interruption; and the generated sleep quality index; and a user interface configured to report the generated sleep quality index and the interruptibility measure.

2. The system of claim 1, wherein the patient waveform is a cardiovascular waveform or a respiratory waveform.

3. The system of claim 1, wherein the instructions, which when executed by the processor, further cause the processor to generate, based on the generated sleep quality index, an intervention measure or prediction based on one or more of the patient's sleep stage and the patient's sleep quality index.

4. The system of claim 1, wherein the generated sleep quality index is a numerical value between 0 and 1 or between 0 and 100, inclusive.

5. The system of claim 1, wherein the instructions, which when executed by the processor, further cause the processor to integrate the generated sleep quality index with additional patient data to generate integrated data.

6. The system of claim 1, wherein the instructions, when executed by the processor, further cause the processor to modify a treatment plan for the patient based on a classified sleep stage.

7. The system of claim 1, wherein the instructions, when executed by the processor, further cause the processor to identify a treatment plan for the patient based on the generated sleep quality index.

8. The system of claim 1, wherein the instructions, when executed by the processor, further cause the processor to identify an environmental factor affecting a patient's sleep quality based on the generated sleep quality index and/or on a plurality of classified sleep stages.

9. A computerized method for monitoring a patient's sleep, the method comprising:
providing a sleep monitoring system comprising: (i) a patient monitor configured to obtain a patient waveform comprising information representative of a vital statistic of a patient; (ii) a processor in communication with the patient monitor; and (iii) a user interface;
receiving, by the processor, the patient waveform from the patient monitor;
processing, by the processor, the patient waveform to generate a segmented waveform;
extracting, by the processor, at least one feature from a segment of the patient waveform in a time domain and/or extracting, by the processor, at least one feature from the segment of the patient waveform in a frequency domain;
classifying, by the processor using the at least one extracted feature, a sleep stage of the patient for the segment of the patient waveform;
generating, by the processor from classified sleep stages for a plurality of segments of the patient waveform, a sleep quality index;

generating, by the processor, an interruptibility measure comprising an objective number of current interruptibility using one or more of: the sleep stage of the patient; a predicted sleep stage; necessity of a patient sleep interruption; and the generated sleep quality index; and reporting, via the user interface, the generated sleep quality index and interruptibility index.

10. The method of claim 9, wherein the method further comprises modifying, based on a classified sleep stage, a treatment for the patient.

11. The method of claim 9, wherein the method further comprises identifying, based on the generated sleep quality index, a treatment for the patient.

12. The method of claim 9, wherein the method further comprises identifying, based on the generated sleep quality index and/or on a plurality of classified sleep stages, an environmental factor affecting a patient's sleep quality.

13. The method of claim 9, wherein the method further comprises integrating the generated sleep quality index with additional patient data to generate integrated data.

14. The method of claim 9, wherein the patient waveform is a cardiovascular waveform or a respiratory waveform.

15. The method of claim 9, wherein the method further comprises generating, based on the generated sleep quality index, an intervention measure or prediction based on one or more of the patient's sleep stage and the sleep quality index.

16. The method of claim 9, wherein the generated sleep quality index is reported as a numerical value between 0 and 1, inclusive.

17. The method of claim 9, wherein the generated sleep quality index is reported graphically.

18. The method of claim 9, wherein the reporting comprises reporting a classified sleep stage or a hypnogram.

19. A tangible, non-transitory computer-readable medium that stores instructions, which when executed by a processor, cause processor to
(i) process a patient waveform to generate a segmented waveform; (ii) extract at least one feature from a segment of the patient waveform in a time domain and/or at least one feature from the segment of the patient waveform in a frequency domain; (iii) classify, using the at least one extracted feature, a sleep stage of a patient for the segment of the patient waveform; (iv) generate, from classified sleep stages for a plurality of segments of the patient waveform, a sleep quality index; and (v) generate an interruptibility measure comprising an objective number of current interruptibility based on one or more of: the sleep stage of the patient; a predicted sleep stage; necessity of a patient sleep interruption; and the generated sleep quality index.

20. The tangible, non-transitory computer-readable medium of claim 19, wherein the instructions, when executed by the processor, further cause the processor to modify a treatment plan for the patient based on a classified sleep stage.

21. The tangible, non-transitory computer-readable medium of claim 19, wherein the instructions, when executed by the processor, further cause the processor to identify a treatment plan for the patient based on the generated sleep quality index.

22. The tangible, non-transitory computer-readable medium of claim 19, wherein the instructions, when executed by the processor, further cause the processor to identify an environmental factor affecting a patient's sleep quality based on the generated sleep quality index and/or on a plurality of classified sleep stages.

23. A system for monitoring a patient's sleep, the system comprising:
 a patient monitor configured to obtain a patient waveform, the patient waveform comprising information representative of a vital statistic of a patient;
 a tangible, non-transitory computer-readable medium that stores instructions;
 a processor in communication with the patient monitor and adapted to execute the instructions to: (i) process the patient waveform to generate a segmented waveform; (ii) extract at least one feature from a segment of the patient waveform in a time domain and/or at least one feature from the segment of the patient waveform in a frequency domain; (iii) classify, using the at least one extracted feature, a sleep stage of the patient for the segment of the patient waveform; (iv) generate, from classified sleep stages for a plurality of segments of the patient waveform, a sleep quality index; and (v) generate an interruptibility measure comprising an objective number of current interruptibility from one or more of: a countdown, a timer, or a predicted time frame indicative of when the patient is more likely to be receptive to interruptions, or when interruptions are less likely to impact a sleep stage index and/or a sleep quality index; and a hypnogram, which characterizes sleep stage dynamics during a recent period of time; and
 a user interface configured to report the generated sleep quality index and the interruptibility measure.

24. The system of claim 23, wherein the patient waveform is a cardiovascular waveform or a respiratory waveform.

25. The system of claim 23, wherein the instructions, which when executed by the processor, further cause the processor to generate, based on the generated sleep quality index, an intervention measure or prediction based on one or more of the patient's sleep stage and the patient's sleep quality index.

26. The system of claim 23, wherein the generated sleep quality index is a numerical value between 0 and 1 or between 0 and 100, inclusive.

27. The system of claim 23, wherein the instructions, which when executed by the processor, further cause the processor to integrate the generated sleep quality index with additional patient data to generate integrated data.

28. The system of claim 23, wherein the instructions, when executed by the processor, further cause the processor to modify a treatment plan for the patient based on a classified sleep stage.

29. The system of claim 23, wherein the instructions, when executed by the processor, further cause the processor to identify a treatment plan for the patient based on the generated sleep quality index.

30. The system of claim 23, wherein the instructions, when executed by the processor, further cause the processor to identify an environmental factor affecting a patient's sleep quality based on the generated sleep quality index and/or on a plurality of classified sleep stages.

* * * * *